US010384045B2

(12) United States Patent
Ding et al.

(10) Patent No.: US 10,384,045 B2
(45) Date of Patent: Aug. 20, 2019

(54) MICROARRAY WITH POLYMER-FREE MICROSTRUCTURES, METHODS OF MAKING, AND METHODS OF USE

(71) Applicant: Corium International, Inc., Menlo Park, CA (US)

(72) Inventors: Zhongli Ding, Sunnyvale, CA (US); Guohua Chen, Sunnyvale, CA (US); Parminder Singh, Union City, CA (US)

(73) Assignee: Corium, Inc., Menlo Park, CA (US)

( * ) Notice: Subject to any disclaimer, the term of this patent is extended or adjusted under 35 U.S.C. 154(b) by 515 days.

(21) Appl. No.: 14/203,429

(22) Filed: Mar. 10, 2014

(65) Prior Publication Data

US 2014/0276474 A1    Sep. 18, 2014

Related U.S. Application Data

(60) Provisional application No. 61/792,715, filed on Mar. 15, 2013.

(51) Int. Cl.
  *A61M 35/00*    (2006.01)
  *A61B 17/20*    (2006.01)
  *A61K 9/00*    (2006.01)

(52) U.S. Cl.
  CPC ........... *A61M 35/00* (2013.01); *A61B 17/205* (2013.01); *A61K 9/0021* (2013.01)

(58) Field of Classification Search
  None
  See application file for complete search history.

(56) References Cited

U.S. PATENT DOCUMENTS

| | | |
|---|---|---|
| 1,554,510 A | 9/1925 | Kirby |
| 1,770,632 A | 7/1930 | Smith |
| 2,046,240 A | 6/1936 | Bayley |
| 2,434,407 A | 1/1948 | George |
| 3,675,766 A | 7/1972 | Rosenthal |
| 3,704,194 A | 11/1972 | Harrier |
| 3,814,097 A | 6/1974 | Ganderton et al. |
| 3,873,255 A | 3/1975 | Kalwaites |
| 3,918,449 A | 11/1975 | Pistor |
| 3,964,482 A | 6/1976 | Gerstel et al. |
| 4,055,029 A | 10/1977 | Kalbow |
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,660,721 A | 4/1987 | Mykleby |
| 4,695,422 A | 9/1987 | Curro et al. |
| 4,743,234 A | 5/1988 | Leopoldi et al. |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,996,159 A | 2/1991 | Glaser |
| 5,051,259 A | 9/1991 | Olsen et al. |
| 5,061,258 A | 10/1991 | Martz |
| 5,134,079 A | 7/1992 | Cusak et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |

(Continued)

FOREIGN PATENT DOCUMENTS

| | | |
|---|---|---|
| CA | 2205444 | 6/1996 |
| CA | 2376285 | 12/2000 |

(Continued)

OTHER PUBLICATIONS

Lutrol® F 68 NF, as accessed from the Internet on Sep. 5, 2016, available from http://www2.basf.us/Pharma/pdf/Lutrol_F_68.pdf.*
"Eudragit EPO Readymix—Taste masking and moisture protection have never been easier" Evonik Industries, Evonik Industries AG, Pharma Polymers & Services, Nov. 2014.
International Search Report from International Patent Application No. PCT/US2014/022836 dated May 9, 2015.
Avcin et al., "Subcutaneous nodule after vaccination with an aluminum-containing vaccina", Acta Dermatoven, APA, vol. 17, No. 4, pp. 182-184 (2008).
Corbett et al., "Skin vaccination against cervical cancer associated human papillomavirus with a novel micro-projection array in a mouse model", PLOS one,vol. 5, No. 10, pp. 1-9 (2010).

(Continued)

*Primary Examiner* — David J Blanchard
*Assistant Examiner* — Daniel F. Coughlin
(74) *Attorney, Agent, or Firm* — McDermott Will & Emery LLP; Judy M. Mohr

(57) ABSTRACT

A microprojection array comprising an approximately planar base and a plurality of microprojections, wherein the array comprises a therapeutic macromolecule and a stabilizing excipient. Described herein are microstructures having a proximal and distal layer, wherein the distal layer which contains the therapeutic molecule does not rely on the presence of a structure-forming polymer to impart the mechanical strength necessary to penetrate the skin. Methods of forming the array, and methods of using the array are contemplated.

18 Claims, 2 Drawing Sheets

(56) References Cited

U.S. PATENT DOCUMENTS

| | | |
|---|---|---|
| 5,163,918 A | 11/1992 | Righi et al. |
| 5,190,558 A | 3/1993 | Matsushita et al. |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabineau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,287 A | 6/1996 | Miskinyar |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,569,469 A | 10/1996 | Lovrechich |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Ericksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,868,244 A | 2/1999 | Ivanov et al. |
| 5,873,849 A | 2/1999 | Bernard |
| 5,879,326 A | 3/1999 | Godshall et al. |
| 5,900,252 A | 5/1999 | Calanchi et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |
| 6,055,453 A | 4/2000 | Hofmann et al. |
| 6,080,172 A | 6/2000 | Fujiwara et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,248,120 B1 | 6/2001 | Wyszogrodzki |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kleiner et al. |
| 6,379,324 B1 | 4/2002 | Garstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,476,288 B1 | 11/2002 | Van Rijswijck et al. |
| 6,485,470 B2 | 11/2002 | Hostettler et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,512,626 B1 | 1/2003 | Schmidt |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whitson |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Garstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |

(56) References Cited

U.S. PATENT DOCUMENTS

| | | |
|---|---|---|
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 6,991,809 B2 | 1/2006 | Anderson |
| 7,011,844 B2 | 3/2006 | Gale et al. |
| 7,048,723 B1 | 5/2006 | Frazier et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,128,730 B2 | 10/2006 | Marano-Ford et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,419,481 B2 | 9/2008 | Trautman et al. |
| 7,572,405 B2 | 8/2009 | Sherman et al. |
| 7,578,954 B2 | 8/2009 | Gartstein et al. |
| 7,578,985 B2 | 8/2009 | Gartstein et al. |
| 7,611,481 B2 | 11/2009 | Cleary et al. |
| 7,658,728 B2 | 2/2010 | Yuzhakov |
| 7,678,777 B2 | 3/2010 | Yasuda et al. |
| 7,763,203 B2 | 7/2010 | Arias et al. |
| 7,785,301 B2 | 8/2010 | Yuzhakov |
| 7,789,733 B2 | 9/2010 | Sugimura |
| 7,798,987 B2 | 9/2010 | Trautman et al. |
| 7,828,827 B2 | 11/2010 | Gartstein et al. |
| 7,846,488 B2 | 12/2010 | Johnson |
| 7,914,480 B2 | 3/2011 | Cleary et al. |
| 8,057,842 B2 | 11/2011 | Choi et al. |
| 8,062,573 B2 | 11/2011 | Kwon |
| 8,216,190 B2 | 7/2012 | Gartstein et al. |
| 8,267,889 B2 | 9/2012 | Cantor et al. |
| 8,366,677 B2 | 2/2013 | Kaspar et al. |
| 8,696,638 B2 | 4/2014 | Terahara et al. |
| 8,702,726 B2 | 4/2014 | Gartstein et al. |
| 8,734,697 B2 | 5/2014 | Chen et al. |
| 8,747,362 B2 | 6/2014 | Terahara |
| 8,771,781 B2 | 7/2014 | Tokumoto et al. |
| 8,821,446 B2 | 9/2014 | Trautman et al. |
| 8,834,423 B2 | 9/2014 | Falo, Jr. et al. |
| 8,900,180 B2 | 12/2014 | Wolter et al. |
| 8,911,749 B2 | 12/2014 | Gharty-Tagoe et al. |
| 9,114,238 B2 | 8/2015 | Singh et al. |
| 9,220,678 B2 | 12/2015 | Kendall et al. |
| 9,452,280 B2 | 9/2016 | Singh et al. |
| 9,498,524 B2 | 11/2016 | Ghartey-Tagoe et al. |
| 9,549,746 B2 * | 1/2017 | Woolfson |
| 9,687,640 B2 | 6/2017 | Trautman et al. |
| 9,687,641 B2 | 6/2017 | Singh et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0123675 A1 | 9/2002 | Trautman et al. |
| 2002/0128599 A1 | 9/2002 | Cormier et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0188310 A1 | 12/2002 | Seward et al. |
| 2002/0193729 A1 | 12/2002 | Cormier et al. |
| 2002/0193819 A1 | 12/2002 | Porter et al. |
| 2003/0083645 A1 | 5/2003 | Angel et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0049150 A1 | 3/2004 | Dalton et al. |
| 2004/0053894 A1 | 3/2004 | Mazess et al. |
| 2004/0062813 A1 | 4/2004 | Cormier et al. |
| 2004/0087893 A1 | 5/2004 | Kwon |
| 2004/0087992 A1 | 5/2004 | Gartstein et al. |
| 2004/0096455 A1 | 5/2004 | Maa et al. |
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1 | 3/2005 | Wong et al. |
| 2005/0065463 A1 | 3/2005 | Tobinga et al. |
| 2005/0089554 A1 | 4/2005 | Cormier et al. |
| 2005/0090803 A1 | 4/2005 | Sherman et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2005/0256045 A1 | 11/2005 | Ameri et al. |
| 2005/0261631 A1 | 11/2005 | Clarke et al. |
| 2005/0271684 A1 | 12/2005 | Trautman et al. |
| 2006/0024358 A1 | 2/2006 | Santini et al. |
| 2006/0067943 A1 | 3/2006 | Maa et al. |
| 2006/0076718 A1 | 4/2006 | Sherman et al. |
| 2006/0095061 A1 | 5/2006 | Trautman et al. |
| 2006/0108914 A1 | 5/2006 | Young |
| 2006/0129174 A1 | 6/2006 | Gartstein et al. |
| 2006/0134188 A1 | 6/2006 | Podhaisky et al. |
| 2006/0149297 A1 | 7/2006 | Sherman et al. |
| 2006/0253079 A1 | 11/2006 | McDonough et al. |
| 2007/0027427 A1 | 2/2007 | Trautman et al. |
| 2007/0191761 A1 | 8/2007 | Boone et al. |
| 2007/0255251 A1 | 11/2007 | Panchula et al. |
| 2008/0009811 A1 | 1/2008 | Cantor |
| 2008/0009825 A1 | 1/2008 | Ringsred et al. |
| 2008/0039805 A1 | 2/2008 | Frederickson et al. |
| 2008/0114298 A1 | 5/2008 | Cantor et al. |
| 2008/0125743 A1 | 5/2008 | Yuzhakov |
| 2008/0183144 A1 | 7/2008 | Trautman et al. |
| 2008/0188771 A1 | 8/2008 | Boecker et al. |
| 2008/0195035 A1 | 8/2008 | Frederickson et al. |
| 2008/0203146 A1 | 8/2008 | Brandwein et al. |
| 2008/0208134 A1 | 8/2008 | Tomono |

(56) References Cited

U.S. PATENT DOCUMENTS

| | | | |
|---|---|---|---|
| 2008/0214987 A1 | 9/2008 | Xu | |
| 2008/0221532 A1 | 9/2008 | Ogawa | |
| 2008/0269685 A1* | 10/2008 | Singh | A61K 9/0021 604/173 |
| 2009/0017210 A1 | 1/2009 | Andrianov et al. | |
| 2009/0035446 A1 | 2/2009 | Kwon | |
| 2009/0041810 A1 | 2/2009 | Andrianov et al. | |
| 2009/0043279 A1 | 2/2009 | Kaspar et al. | |
| 2009/0155330 A1 | 6/2009 | Ghartey-Tagoe et al. | |
| 2009/0182306 A1* | 7/2009 | Lee | A61K 9/0021 604/506 |
| 2009/0216215 A1 | 8/2009 | Thalmann et al. | |
| 2010/0028390 A1 | 2/2010 | Cleary et al. | |
| 2010/0200494 A1 | 8/2010 | Storer | |
| 2010/0228203 A1 | 9/2010 | Quan et al. | |
| 2010/0247698 A1 | 9/2010 | Zhang et al. | |
| 2011/0006458 A1 | 1/2011 | Sagi et al. | |
| 2011/0028905 A1 | 2/2011 | Takada | |
| 2011/0046638 A1 | 2/2011 | Gartstein et al. | |
| 2011/0059150 A1 | 3/2011 | Kendall et al. | |
| 2011/0098651 A1 | 4/2011 | Falo et al. | |
| 2011/0121486 A1 | 5/2011 | Oh et al. | |
| 2011/0160069 A1 | 6/2011 | Corrie et al. | |
| 2011/0165236 A1 | 7/2011 | Chow et al. | |
| 2011/0177139 A1 | 7/2011 | Hyungil et al. | |
| 2011/0276027 A1 | 11/2011 | Trautman et al. | |
| 2011/0276028 A1 | 11/2011 | Singh et al. | |
| 2011/0280800 A1* | 11/2011 | Wu | A61K 9/0019 424/1.49 |
| 2011/0288484 A1 | 11/2011 | Kendall et al. | |
| 2011/0288485 A1 | 11/2011 | Tokumoto et al. | |
| 2011/0295205 A1 | 12/2011 | Kaufmann et al. | |
| 2011/0306853 A1 | 12/2011 | Black et al. | |
| 2012/0052120 A1 | 3/2012 | Castor | |
| 2012/0123297 A1 | 5/2012 | Brancazio | |
| 2012/0123387 A1 | 5/2012 | Gonzalez et al. | |
| 2012/0130306 A1 | 5/2012 | Terahara et al. | |
| 2012/0150023 A1 | 6/2012 | Kaspar et al. | |
| 2012/0184906 A1 | 7/2012 | McAllister | |
| 2012/0330250 A1 | 12/2012 | Kuwahara et al. | |
| 2013/0131598 A1 | 5/2013 | Trautman et al. | |
| 2013/0150822 A1 | 6/2013 | Ross | |
| 2013/0287832 A1 | 10/2013 | O'Hagan et al. | |
| 2013/0292868 A1 | 11/2013 | Singh et al. | |
| 2013/0292886 A1 | 11/2013 | Sagi et al. | |
| 2013/0303502 A1 | 11/2013 | Cavanagh et al. | |
| 2014/0148846 A1 | 5/2014 | Pereira et al. | |
| 2014/0180201 A1 | 6/2014 | Ding et al. | |
| 2014/0248312 A1 | 9/2014 | Rappuoli et al. | |
| 2014/0257188 A1 | 9/2014 | Kendall et al. | |
| 2014/0272101 A1 | 9/2014 | Chen et al. | |
| 2014/0276366 A1 | 9/2014 | Bourne et al. | |
| 2014/0276378 A1 | 9/2014 | Chen et al. | |
| 2014/0276474 A1 | 9/2014 | Ding et al. | |
| 2014/0276580 A1 | 9/2014 | Le et al. | |
| 2014/0276589 A1 | 9/2014 | Bayramov et al. | |
| 2014/0330198 A1 | 11/2014 | Zhang et al. | |
| 2015/0079133 A1 | 3/2015 | Ghartey-Tagoe et al. | |
| 2015/0238413 A1 | 8/2015 | Mochizuki et al. | |
| 2015/0297878 A1 | 10/2015 | Singh et al. | |
| 2016/0058992 A1 | 3/2016 | Chen et al. | |
| 2016/0067176 A1 | 3/2016 | Ding et al. | |
| 2016/0135895 A1 | 5/2016 | Faasse et al. | |
| 2016/0175572 A1 | 6/2016 | Crowley et al. | |
| 2016/0374939 A1 | 12/2016 | Shastry et al. | |
| 2017/0050010 A1 | 2/2017 | Mcallister et al. | |
| 2017/0281535 A1 | 10/2017 | Singh et al. | |
| 2017/0361079 A1 | 12/2017 | Trautman et al. | |

FOREIGN PATENT DOCUMENTS

| | | |
|---|---|---|
| CA | 2316534 | 3/2001 |
| CA | 2422907 | 4/2002 |
| CA | 2889500 A1 | 5/2014 |
| CN | 102000020 A | 6/2011 |
| CN | 102580232 A | 7/2012 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0305123 A1 | 3/1989 |
| EP | 0312662 | 4/1989 |
| EP | 0400249 | 12/1990 |
| EP | 0407063 | 1/1991 |
| EP | 0796128 | 9/1997 |
| EP | 1086718 A1 | 3/2001 |
| EP | 1086719 A1 | 3/2001 |
| EP | 1174078 | 1/2002 |
| EP | 2283809 A1 | 2/2011 |
| EP | 2399624 A1 | 12/2011 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-000728 A | 1/2002 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2003-534881 A | 11/2003 |
| JP | 2004-065775 A | 3/2004 |
| JP | 2007-190112 A | 1/2006 |
| JP | 2006/271781 A | 10/2006 |
| JP | 2006-341089 A | 12/2006 |
| JP | 2007-130030 A | 5/2007 |
| JP | 2007-536988 A | 12/2007 |
| JP | 2008-006178 A | 1/2008 |
| JP | 2008-074763 A | 4/2008 |
| JP | 2008-194288 A | 8/2008 |
| JP | 2009-082206 A | 4/2009 |
| JP | 2009-082207 A | 4/2009 |
| JP | 2009-201956 A | 9/2009 |
| JP | 2010-233673 A | 10/2010 |
| JP | 2010-233674 A | 10/2010 |
| KR | 20100064669 A | 6/2010 |
| RU | 2414255 C1 | 3/2011 |
| SU | 1641346 | 4/1991 |
| SU | 1667864 | 8/1991 |

(56) References Cited

FOREIGN PATENT DOCUMENTS

| | | |
|---|---|---|
| WO | WO 1993/015701 | 8/1993 |
| WO | WO 1993/017754 | 9/1993 |
| WO | WO 1994/023777 | 10/1994 |
| WO | WO 1995/022612 | 8/1995 |
| WO | WO 1995/033612 | 12/1995 |
| WO | WO 1996/000109 | 1/1996 |
| WO | WO 1996/017648 | 6/1996 |
| WO | WO 1996/037155 | 11/1996 |
| WO | WO 1996/037256 | 11/1996 |
| WO | WO 1997/003629 | 2/1997 |
| WO | WO 1997/003718 | 2/1997 |
| WO | WO 1997/013544 | 4/1997 |
| WO | WO 1997/048440 | 12/1997 |
| WO | WO 1997/048441 | 12/1997 |
| WO | WO 1997/048442 | 12/1997 |
| WO | WO 1998/000193 | 1/1998 |
| WO | WO 1998/028307 | 7/1998 |
| WO | WO 1999/000155 | 1/1999 |
| WO | WO 1999/029298 | 6/1999 |
| WO | WO 1999/029364 | 6/1999 |
| WO | WO 1999-029365 | 6/1999 |
| WO | WO 1999/049874 A1 | 10/1999 |
| WO | WO 1999/061888 | 12/1999 |
| WO | WO 1999/064580 | 12/1999 |
| WO | WO 2000/005166 | 2/2000 |
| WO | WO 2003/026733 A2 | 4/2000 |
| WO | WO 2000/035530 | 6/2000 |
| WO | WO 2000/070406 | 11/2000 |
| WO | WO 2000/074763 A2 | 12/2000 |
| WO | WO 2000/074764 | 12/2000 |
| WO | WO 2000/074765 | 12/2000 |
| WO | WO 2000/074766 | 12/2000 |
| WO | WO 2000/077571 | 12/2000 |
| WO | WO 2001/008242 | 2/2001 |
| WO | WO 2001/036037 | 5/2001 |
| WO | WO 2001/036321 | 5/2001 |
| WO | WO 2001/049362 | 7/2001 |
| WO | WO 2002/002180 | 1/2002 |
| WO | WO 2002/007543 | 1/2002 |
| WO | WO 2002/007813 | 1/2002 |
| WO | WO 2002/017985 | 3/2002 |
| WO | WO 2002/030301 A1 | 4/2002 |
| WO | WO 2002/032331 | 4/2002 |
| WO | WO 2002/032480 | 4/2002 |
| WO | WO 2002/062202 | 8/2002 |
| WO | WO 2002/064193 A2 | 8/2002 |
| WO | WO 2002/072189 | 9/2002 |
| WO | WO 2002/085446 A2 | 10/2002 |
| WO | WO 2002/091922 | 11/2002 |
| WO | WO 2002/100474 | 12/2002 |
| WO | WO 2003/024290 | 3/2003 |
| WO | WO 2003/024518 | 3/2003 |
| WO | WO 2004/000389 A2 | 12/2003 |
| WO | WO 2004/009172 A1 | 1/2004 |
| WO | WO 2004/024224 A1 | 3/2004 |
| WO | WO 2004/030649 A2 | 4/2004 |
| WO | WO 2004/076339 | 9/2004 |
| WO | WO 2004/105729 A2 | 12/2004 |
| WO | WO 2004/110717 | 12/2004 |
| WO | WO 2005/002453 A1 | 1/2005 |
| WO | WO 2005/046769 A2 | 5/2005 |
| WO | WO 2005/065765 A1 | 7/2005 |
| WO | WO 2005/082596 A1 | 9/2005 |
| WO | WO 2005/089857 A1 | 9/2005 |
| WO | WO 2005/094526 | 10/2005 |
| WO | WO 2005/099751 A2 | 10/2005 |
| WO | WO 2005/112984 A2 | 12/2005 |
| WO | WO 2006/020842 | 2/2006 |
| WO | WO 2006/056795 | 5/2006 |
| WO | WO 2006/062848 A1 | 6/2006 |
| WO | WO 2006/086742 A2 | 8/2006 |
| WO | WO 2006/101459 A1 | 9/2006 |
| WO | WO 2007/002521 A2 | 1/2007 |
| WO | WO 2007/002522 A1 | 1/2007 |
| WO | WO 2007/002523 | 1/2007 |
| WO | WO 2007/012114 A1 | 2/2007 |
| WO | WO 2007/030477 A2 | 3/2007 |
| WO | WO 2007/061964 A1 | 5/2007 |
| WO | WO 2007/061972 A2 | 5/2007 |
| WO | WO 2007/075806 A2 | 7/2007 |
| WO | WO 2007/081430 A2 | 7/2007 |
| WO | WO 2007/124411 | 11/2007 |
| WO | WO 2008/011625 | 1/2008 |
| WO | WO 2008/015236 A1 | 2/2008 |
| WO | WO 2008/024141 A2 | 2/2008 |
| WO | WO 2008/091602 | 7/2008 |
| WO | WO 2008/130587 | 10/2008 |
| WO | WO 2008/139648 A1 | 11/2008 |
| WO | WO 2009/039013 A1 | 3/2009 |
| WO | WO 2009/048607 A1 | 4/2009 |
| WO | WO 2009/054988 A1 | 4/2009 |
| WO | WO 2009/142741 A1 | 11/2009 |
| WO | WO 2010/040271 A1 | 4/2010 |
| WO | WO 2010/124255 A2 | 10/2010 |
| WO | WO 2011/121023 A1 | 10/2011 |
| WO | WO 2011/140240 | 10/2011 |
| WO | WO 2011/140274 | 10/2011 |
| WO | WO 2012/153266 A2 | 1/2012 |
| WO | WO 2012/054582 A2 | 4/2012 |
| WO | WO 2012/122163 A1 | 9/2012 |
| WO | WO 2012/127249 A1 | 9/2012 |
| WO | WO 2013/172999 A1 | 11/2013 |
| WO | WO 2014/004301 A1 | 1/2014 |
| WO | WO 2014/077244 A1 | 5/2014 |
| WO | WO 2014/100750 A1 | 6/2014 |
| WO | WO 2014/144973 A1 | 9/2014 |
| WO | WO 2014/150069 A1 | 9/2014 |
| WO | WO 2014/150285 A2 | 9/2014 |
| WO | WO 2014/151654 A1 | 9/2014 |
| WO | WO 2014/164314 A1 | 10/2014 |
| WO | WO 2016/033540 A1 | 3/2016 |
| WO | WO 2016/036866 A1 | 3/2016 |
| WO | WO 2016/073908 A1 | 5/2016 |
| WO | WO 2017/004067 A1 | 1/2017 |

OTHER PUBLICATIONS

Database WPI / Thomson, Accession No. 2014-V89218, Gao et al., "Soluble microneedle patch useful for transdermal administration of vaccine, comprises water-soluble polymer material as matrix material and soluble microneedle main portion", Application No. CN104027324A, Tech Inst Phys. & Chem. Chinese Acad., 3 pages (2014).

Ghosh et al., "Influence of critical parameters of nanosuspension formulation on permeability of a poorly soluble drug through the skin-A case study", vol. 14, No. 3, pp, 1108-1117 (2013).

Guo et al., "Enhanced transcutaneous immunization via dissolving microneedle array loaded with liposome encapsulated antigen and adjuvant", Int. J. Pharm., vol. 447, No. 1-2, pp. 22-30 (2013).

Gupta, "Aluminum compounds as vaccine adjuvants", Adv. Drug Deliv. Rev., vol. 32, No. 3, pp. 155-172 (1998) Abstract Only.

Gupta and Rost, "Aluminum compounds as vaccine adjuvants", Vaccine adjuvants: Preparation Methods and Research Protocols, O'Hagan, ed., Humana Press, Inc., Totowa, New Jersey, Meth. Mol. Med., vol. 42, No. 4, No. 4, pp. 65-89 (2000).

International Search Report from International Patent Application No. PCT/US2015/047563 dated Nov. 20, 2015.

International Search Report from International Patent Application No. PCT/US2015/048161 dated Nov. 26, 2015.

Kuroda et al., "Particulate adjuvant and innate immunity: past achievements, present findings, and future prospects", Int. Rev. Immunol., vol. 32, No. 2, pp. 209-220 (2013).

Munks et al., "Aluminum adjuvants elicit fibrin-dependent extracellular traps in vivo", Blood, vol. 116, No. 24, pp. 5191-5199 (2010).

Petrovsky and Aguilar, "Vaccine adjuvants: current state and future trends", Immunol. Cell Biol., vol. 82, No. 5, pp. 488-496 (2004).

Pittman, "Aluminum-containing vaccine associated adverse events: role of route of administration and gender", Vaccine, vol. 20, pp. s48-s50 (2002).

(56) References Cited

OTHER PUBLICATIONS

Prausnitz, "Microneedie-based vaccines", Curr. Top. Microbiol. Immunol., vol. 333, pp. 369-393 (2009).
Sayers et al., "Vaxjo: A Web-Based Vaccine Adjuvant Database and Its Application for Analysis of Vaccine Adjuvants and Their Uses in Vaccine Development", J. Biomed. Biotechnol., vol. 2012, Article ID: 831486, 13 pages, doi:10.1155/2012/831486 (2011).
White et al., "Studies on antibody production. III. The alum granuloma", J. Exp. Med., vol. 102, No. 1, pp. 73-82 (1955).
International Search Report from International Patent Application No. PCT/US2015/059559 dated Jan. 21, 2016.
Keitel et al., "A randomized clinical trail of acellular pertussis vaccines in healthy adults: Dose-response comparisons of 5 vaccines and implications for booster immunization", J. Infect. Dis., vol. 180, pp. 397-403 (1999).
Vitiello et al., "Development of a lipopeptide-based therapeutic vaccine to treat chronic HBV infection", J. Clin. Invest., vol. 95, pp. 341-349 (1995).
International Search Report from International Patent Application No. PCT/US2014/021841 dated Aug. 11, 2014.
International Search Report from International Patent Application No. PCT/US2014/026179 dated Jul. 18, 2014.
International Search Report from International Patent Application No. PCT/US2014/029601 dated Jul. 1, 2014.
Chun, et al., "An array of hollow microcapiliaries for the controlled injection of genetic materials into animal/plant cells." IEEE Workshop on Micro Electro Mechanical Systems, pp. 406-411, (1999).
"Extend", Merriam-Webster Online Dictionary, 6 pages, Downloaded on Sep. 7, 2010 from <http://www.merriam-webster.com/dictionary/extend>.
"Extend", Macmillan Online Dictionary, 5 pages, Downloaded on Sep. 7, 2010 from <http://www.macmillandictionary.com/dictionary/american/extend>.
Henry, et al., "Micromachined microneedles for transdermal delivery of drugs", IEEE Workshop on Micro Electro Mechanical Systems, New York, NY, pp. 494-498, (1998).
Henry, et al., "Microfabricated microneedles: A novel approach to transdermal drug delivery", J. Pharmaceutical Science, vol. 87, No. 8, pp. 922-925, (1998).
"Heparin Pregnancy and Breast Feeding Warnings", Drugs.com, Accessed Oct. 8, 2009, <http://www.drugs.com/pregnancy/heparin.html>.
International Search Report from International Patent Application No. PCT/US2000/015612 dated Sep. 7, 2000.
International Search Report from International Patent Application No. PCT/US2000/015613 dated Sep. 6, 2000.
International Search Report from International Patent Application No. PCT/US2000/015614 dated Sep. 6, 2000.
International Search Report from International Patent Application No. PCT/US2001/031977 dated Apr. 29, 2002.
International Search Report from International Patent Application No. PCT/US2001/031978 dated Apr. 29, 2002.
International Search Report from International Patent Application No. PCT/US2002/014624 dated Sep. 3, 2002.
International Search Report from International Patent Application No. PCT/US2002/029228 dated Apr. 23, 2003.
International Search Report from International Patent Application No. PCT/US2002/029245 dated Dec. 27, 2002.
International Search Report from International Patent Application No. PCT/US2004/005382 dated Nov. 25, 2004.
International Search Report from International Patent Application No. PCT/US2004/017255 dated May 24, 2005.
International Search Report from International Patent Application No. PCT/US2005/009854 dated Jul. 3, 2008.
International Search Report from International Patent Application No. PCT/US2008/000824 dated Jul. 18, 2008.
International Search Report from International Patent Application No. PCT/US2008/004943 dated Jun. 9, 2009, application now published as International Publication No. WO2008/130587 dated Oct. 30, 2008.
International Search Report from International Patent Application No. PCT/US2008/011635 dated Dec. 19, 2008, application now published as International Publication No. WO2009/048607 dated Apr. 16, 2009.
International Search Report from International Patent Application No. PCT/US2010/032299 dated Dec. 10, 2010, application now published as International Publication No. WO2010/124255 dated Oct. 28, 2010.
International Search Report from International Patent Application No. PCT/US2013/077281 dated Mar. 4, 2013.
International Search Report from International Patent Application No. PCT/US2014/022087 dated May 23, 2014.
International Search Report from International Patent Application No. PCT/US2014/022859 dated May 26, 2014.
Matriano, et al., "Macroflux(R) microprojection array patch technology: A new and efficient approach for intracutaneous immunization", Pharm. Res., vol. 19, No. 1, pp. 63-70, (2002).
McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.
Mikszta, et al., "Improvred genetic immunization via micromechanical disruption of skin-barrier function and targeted epidermal delivery", Nat. Med., vol. 8, No. 4, pp. 415-419, (2002).
Mikszta, et al., "Protective immunization against inhalation anthrax: A comparison of minimally invasive delivery platforms", J. Inf. Dis., vol. 191, No. 2, pp. 278-288, (2005).
Papautsky, et al., "Micromachined Pipette Arrays," MPA Proceedings—19th international Conference—IEEE/EMBS, Chicago, IL, USA, pp. 2281-2284 (1997).
Park et al., "Biodegradable polymer microneedles: Fabrication, mechanics, and transdermal drug delivery", J. Contr. Rel., vol. 104, pp. 51-66 (2005).
Park, et al., "Polymer Microneedles for Controlled-Release Drug Delivery," Pharmaceutical Research, Kluwer Academic Publishers-Plenum Publishers, NE, vol. 23, No. 5, pp. 1008-1019 (2006).
Prausnitz, et al., "Transdermal transport efficiency during skin electroporation and iontophoresis", J. Contr. Release, vol. 38, pp. 205-217, (1996).
Prausnitz, "Transdermal delivery of macromolecules: Recent advances by modification of skin's barrier properties", ACS Symposium Series No. 675, *Therapeutic Protein And Peptide Formulation And Delivery*, American Chemical Society, Washington DC, Chapter 8, pp. 124-153, (1997).
Rydberg, et al., "Low-molecular-weight heparin preventing and treating DVT", Am. Fam. Physician, vol. 59, No. 6, pp. 1607-1612, (1999).
Sivamani, et al., "Microneedles and transdermal applications", Exp. Opin. Drug Del., vol. 4, No. 1, pp. 19-25, (2007).
Wouters, et al., "Microelectrochemical systems for drug delivery", Electrochimica Acta., vol. 42, pp. 3385-3390, (1997).
Xia, et al., "Soft Lithography", Agnew. Chem. Int. Ed., vol. 37, pp. 551-575, (1998).
Xia, et al., "Soft Lithography", Annu. Rev. Mater. Sci., vol. 28, pp. 153-184 (1998).
International Search Report from International Patent Application No. PCT/US2011/035221 dated Jan. 10, 2012, application now published as International Publication No. WO2011/140240 dated Nov. 10, 2011.
International Search Report from International Patent Application No. PCT/US2016/039864 dated Sep. 23, 2016.
Makaida et al., "Poly lactic-co-glycolic acid (PLGA) as biodegradable controlled drug delivery carrier", Polymers (Basel), vol. 3 No. 3, pp. 1377-1397 (2011).
Julinova et al., "Initiating biodegradation of polyvinylpyrrolidone in aqueous aerobic environment", Proceedings of ECOpole, vol. 6, No. 1, pp. 121-127 (2012).
Kunduru et al., "Biodegradable polymers: Medical Applications", Encyclopedia of Polymer Science and Technology, pp. 1-22 (2016) DOI: 10.1002/0471440264.pst027.pub2.

(56) References Cited

OTHER PUBLICATIONS

Polysorbate 80, Material Safety Data Sheet, CAS#: 9005-65-6, Science Lab.com, Inc., 14025 Smith Rd., Houston, Texas 77396, 5 pages, Last updated May 21, 2013.

\* cited by examiner

MICROARRAY WITH POLYMER-FREE MICROSTRUCTURES, METHODS OF MAKING, AND METHODS OF USE

CROSS-REFERENCE TO RELATED APPLICATIONS

This application claims the benefit of U.S. Provisional Application No. 61/792,715, filed Mar. 15, 2013, which is incorporated herein by reference in its entirety.

TECHNICAL FIELD

The disclosure relates generally to a method and delivery system for transdermally administering a therapeutic polypeptide using an array of microstructures, and related features thereof.

BACKGROUND

Arrays of microneedles were proposed as a way of administering drugs through the skin in the 1970s, for example in expired U.S. Pat. No. 3,964,482. Microneedle or microstructure arrays can facilitate the passage of drugs through or into human skin and other biological membranes in circumstances where ordinary transdermal administration is inadequate. Microstructure arrays can also be used to sample fluids found in the vicinity of a biological membrane such as interstitial fluid, which is then tested for the presence of biomarkers.

Despite much initial work on fabricating microneedle arrays in silicon or metals, there are significant advantages to polymeric arrays. U.S. Pat. No. 6,451,240 discloses some methods of manufacturing polymeric microneedle arrays. Arrays made primarily of biodegradable polymers also have some advantages. U.S. Pat. No. 6,945,952 and U.S. Published Patent Applications Nos. 2002/0082543 and 2005/0197308 have some discussion of microneedle arrays made of biodegradable polymers. A detailed description of the fabrication of a microneedle array made of polyglycolic acid is found in Jung-Hwan Park et al., "Biodegradable polymer microneedles: Fabrication, mechanics, and transdermal drug delivery," J. of Controlled Release, 104:51-66 (2005).

One increasing popular use for polymeric microneedles and microarrays currently undergoing development involves the use of biodegradable or soluble microneedles or microstructures for subcutaneous delivery of biomolecules. Therapeutic biomolecules showing promise include proteins, peptides and nucleic acids. Protein-based drugs are becoming increasing common and effective in the treatment of several conditions such as cancer and autoimmune diseases such as rheumatoid arthritis. Proteins are large and very complex molecules, having secondary and tertiary structures which usually must be preserved to maintain the therapeutic efficacy of the protein. This complex nature and accompanying stability issues make proteins difficult drug candidates for delivery. Currently, proteins are being predominantly administered by the parenteral route. However, this route of administration usually requires repeated administration due to the short half-life of such molecules. While oral, pulmonary and nasal routes of polypeptide delivery are also under development, these routes have limitations such as gastrointestinal degradation, low bioavailability and local irritation.

Use of transdermal delivery systems which can traverse the stratum corneum barrier and permeate into the deeper layers of the skin is a viable option for administration of therapeutic biologic molecules, including proteins. It has been reported that the skin has relatively low proteolytic activity as compared to mucosal routes. Thereby reducing the amount of protein degradation.

Accordingly, it would be of benefit to develop an effective means of delivering large biomolecules via microstructures and of making use of the advantages of microstructure array delivery.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In a first aspect, an array of microstructures is provided comprising an approximately planar base and a plurality of microstructures comprising a drug, wherein each of the plurality of microstructures has mechanical strength sufficient to provide transdermal administration to a subject. The microstructure comprises a backing having a first surface and a second surface opposed thereto, and a microstructure array comprising the plurality of microstructures, wherein the plurality of microstructures extend outwardly from the first surface of the backing. Each of the plurality of microstructures comprises a biodegradable distal layer and at least one proximal layer positioned between the distal layer and the first surface of the backing. The distal layer comprises at least one drug and a stabilizing excipient.

In one embodiment, each of the plurality of microstructures does not comprise a structural polymer.

In one embodiment, the drug is a therapeutic macromolecule and the at least one therapeutic macromolecule is present in the distal layer in an amount which is about 30% to 90% of the distal layer.

In one embodiment, the at least one therapeutic macromolecule has a molecular weight of at least 20,000 Daltons (Da).

In one embodiment, the macromolecule is a polypeptide. In another embodiment, the macromolecule is a hormone. In still another embodiment, the macromolecule is an antibody or fragment thereof. In yet another embodiment, the macromolecule is a monoclonal antibody.

In one embodiment, the macromolecule is glycosylated.

In one embodiment, the macromolecule has a molecular weight of about 20,000 Da to 100,000 Da, 20,000 Da to 75,000 Da, 40,000 Da to 75,000 Da, 40,000 Da to 100,000 Da, 100,000 Da to 1,000,000 Da, 100,000 Da to 800,000 Da, 100,000 Da to 500,000 Da, 100,000 Da to 300,000 Da, 75,000 Da to 500,000 Da, 300,000 Da to 1,000,000 Da, 500,000 Da to 1,000,000 Da or 300,000 Da to 700,000 Da. In one embodiment, the molecular weight is that in the presence of or the absence of the glycosylation.

In one embodiment, the macromolecule is present in the distal layer at a concentration or amount of about 20% to 95%, 30% to 95%, 40% to 95%, 50% to 95%, 50% to 90%, 50% to 80%, 50% to 75%, 60% to 95%, 60% to 90%, 60% to 80%, 60% to 70%, 75% to 95% or 70% to 90% of the distal layer. In one embodiment, % is weight %.

In one embodiment the stabilizing excipient is a sugar. In another embodiment, the sugar is sucrose or trehalose. In still another embodiment, the sugar is present in each of the plurality of microstructures at a concentration of about 1% to 20%, 5% to 10%, 5% to 15%, 10% to 15% or 10% to 20%. In one embodiment, % is weight %.

In one embodiment, each of the plurality of microstructures comprises a surfactant. In another embodiment, the surfactant is sorbitol. In yet another embodiment, the surfactant is Polysorbate 80 and Polysorbate 20. In still another embodiment, the surfactant is present in each of the plurality of microstructures at a concentration of about 0.001% to 0.1%, 0.001% to 0.01%, 0.005% to 0.1%, 0.005% to 0.01%, 0.01% to 0.1%, 0.01% to 0.5%, 0.01% to 0.1%, 0.01% to 0.05%, or 0.02% to 0.07%, 0.1% to 1.0%, 0.01% to 1.0%, 0.001% to 1.0%, 0.1% to 5.0%, 1.0% to 5.0% of the distal layer. In one embodiment, % is weight %.

In one embodiment, each of the plurality of microstructures comprises an antioxidant. In another embodiment, the antioxidant is ethylenediaminetetraacetic acid (EDTA) or ascorbic acid. In still another embodiment, the antioxidant is present in each of the plurality of microstructures at a concentration of about 0.001% to 0.1%, 0.001% to 0.01%, 0.005% to 0.1%, 0.005% to 0.01%, 0.01% to 0.1%, 0.01% to 0.5%, 0.01% to 0.1%, 0.01% to 0.05%, or 0.02% to 0.07%, 0.1% to 1.0%, 0.01% to 1.0%, 0.001% to 1.0%, 0.1% to 5.0%, 1.0% to 5.0% of the distal layer. In one embodiment, % is weight %.

In a second aspect, method for making a microstructure array is provided, comprising: (a) mixing a polypeptide solution with a stabilizing excipient to form a polypeptide molding solution; (b) dispensing the polypeptide molding solution on a mold having an array of microstructure cavities; (c) filling the microstructure cavities in the mold; (f) removing excess solution or suspension polymer matrix on the mold surface; (g) drying the solution in a chamber having partial pressure of about 50 psi at a temperature of about 5° C. to 50° C.; (h) drying the solution at about 5° C. to 50° C. to form an array of microstructures; and (i) drying the microstructure under vacuum at about 5° C. to 50° C.

In one embodiment, the drying the solution to form an array of microstructures is at about 10° C. to 50° C., 10° C. to 40° C., 10° C. to 30° C., 15° C. to 50° C., 15° C. to 40° C., 15° C. to 30° C., 25° C. to 50° C., 25° C. to 35° C., or 32° C.

In one embodiment, the drying the microstructure under vacuum is at about 10° C. to 50° C., 10° C. to 40° C., 10° C. to 30° C., 15° C. to 50° C., 15° C. to 40° C., 15° C. to 30° C., 25° C. to 50° C., 25° C. to 35° C., or 32° C.

In one embodiment, the drying the basement or backing layer comprises drying in an oven at about 5° C. to 50° C., 10° C. to 50° C., 10° C. to 40° C., 10° C. to 30° C., 15° C. to 50° C., 15° C. to 40° C., 15° C. to 30° C., 25° C. to 50° C., 25° C. to 35° C., 30° C. to 40° C., 37° C., 35° C., or 32° C.

In one embodiment, the chamber uses convection, conduction or radiation for drying.

In one embodiment, the method further comprises (j) dispensing a basement or backing layer on the mold surface; and (k) drying the basement or backing layer.

In one embodiment, the method further comprises affixing the basement or backing layer to a substrate.

In one embodiment, the polypeptide molding solution is lyophilized then resuspended in water containing a surfactant prior to dispensing into the mold.

In a third aspect, a method for making a microstructure array is provided, comprising (a) mixing a polypeptide solution with a stabilizing excipient to form a polypeptide molding solution; (b) dispensing the polypeptide molding solution on a mold having an array of microstructure cavities; (c) filling the microstructure cavities in the mold; (f) removing excess solution or suspension polymer matrix on the mold surface; (g) drying the solution in a chamber having relative humidity of about 10% to 95% at a temperature of about 5° C. to 50° C.; (h) drying the solution at about 5° C. to 50° C. to form an array of microstructures; and (i) drying the microstructure under vacuum at about 5° C. to 50° C.

In one embodiment, the drying to solution in a chamber having humidity is done in a chamber having a relative humidity of about 25% to 90%, 50% to 85%, or 75% to 90%.

In one embodiment, the drying the solution to form an array of microstructures is at about 5° C. to 50° C., 10° C. to 50° C., 10° C. to 40° C., 10° C. to 30° C., 15° C. to 50° C., 15° C. to 40° C., 15° C. to 30° C., 25° C. to 50° C., 25° C. to 35° C., or 32° C.

In one embodiment, the drying the microstructure under vacuum is at about 5° C. to 50° C., 10° C. to 50° C., 10° C. to 40° C., 10° C. to 30° C., 15° C. to 50° C., 15° C. to 40° C., 15° C. to 30° C., 25° C. to 50° C., 25° C. to 35° C., or 32° C.

In one embodiment, drying the basement or backing layer comprises drying in an oven at about 5° C. to 50° C., 10° C. to 50° C., 10° C. to 40° C., 10° C. to 30° C., 15° C. to 50° C., 15° C. to 40° C., 15° C. to 30° C., 25° C. to 50° C., 25° C. to 35° C., or 32° C.

In one embodiment, the chamber uses convection, conduction or radiation for drying.

In one embodiment, the method further comprises: (j) dispensing a basement or backing layer on the mold surface; and (k) drying the basement or backing layer.

In one embodiment, the method further comprises affixing the basement or backing layer to a substrate.

In one embodiment, the polypeptide molding solution is lyophilized then resuspended in water containing a surfactant prior to dispensing into the mold.

In a fourth aspect, a method for administering a therapeutic macromolecule to a mammalian subject is provided, comprising inserting into the skin of the subject a microstructure array as described above.

Additional embodiments of the present microstructures, arrays, methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIG. 2A depicts a microstructure having a pyramidal tip with a funnel shaped distal portion. FIG. 2B depicts a microstructure having a conical tip, a cylindrical shank and a conical funnel distal portion.

Figure 1C:
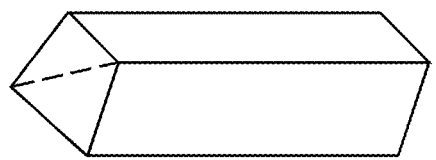
FIGS. 1A-1C are illustrations of exemplary shapes for microstructures of the arrays described herein.

It will be appreciated that the thicknesses and shapes for the various microstructures have been exaggerated in the drawings to facilitate understanding of the device. The drawings are not necessarily "to scale."

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, Biochemistry (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; Goodman & Gilman *The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

I. DEFINITIONS

As used in this specification, the singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

In describing and claiming the present invention, the following terminology will be used in accordance with the definitions described below.

"Optional" or "optionally" means that the subsequently described circumstance may or may not occur, so that the description includes instances where the circumstance occurs and instances where it does not.

"Substantially" or "essentially" means nearly totally or completely, for instance, 90-95% or greater of some given quantity.

"Hydrophobic polymer" as used herein refers to polymers that are insoluble or poorly soluble in aqueous solvents. "Hydrophilic polymer" as used herein refers to polymers that are soluble or substantially soluble in aqueous solvents.

The terms "microprotrusion", "microprojection", "microstructure" or "microneedle" are used interchangeably herein to refer to elements adapted to penetrate or pierce at least a portion of the stratum corneum or other biological membranes. For example, illustrative microstructures may include, in addition to those provided herein, microblades as described in U.S. Pat. No. 6,219,574, edged microneedles as described in U.S. Pat. No. 6,652,478, and microprotrusions as described in U.S. Patent Publication No. U.S. 2008/0269685 and U.S. 2009/0155330.

"Transdermal" refers to the delivery of an agent into and/or through the skin for local and/or systemic therapy. The same inventive principles apply to administration through other biological membranes such as those which line the interior of the mouth, gastro-intestinal tract, blood-brain barrier, or other body tissues or organs or biological membranes which are exposed or accessible during surgery or during procedures such as laparoscopy or endoscopy.

A material that is "water-soluble" may be defined as soluble or substantially soluble in aqueous solvents, such that the material dissolves into, within or below the skin or other membrane which is substantially aqueous in nature.

"Biodegradable" refers to natural or synthetic materials that degrade enzymatically, non-enzymatically or both to produce biocompatible and/or toxicologically safe by-products which may be eliminated by normal metabolic pathways.

The term "antibody" is used in the broadest sense and specifically covers monoclonal antibodies (including agonist and antagonist antibodies), antibody compositions with polyepitopic specificity, and antibody fragments (e.g., Fab, F(ab')$_2$, scFv and Fv), so long as they exhibit the desired biological activity. "Antibody" is meant to include polyclonal antibodies, monoclonal antibodies, humanized antibodies, human antibodies, primatized antibodies and other antibodies produced via genetic engineering.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In addition to their specificity, the monoclonal antibodies are advantageous in that they are synthesized by mammalian cell expression systems or transgenic technology, uncontaminated by other immunoglobulins. For example, the monoclonal antibodies to be used in accordance with the present invention may be expressed in goats, as described by Behboodi, et al. (2002) "Transgenic cloned goats and the production of therapeutic proteins." In *Principles of Cloning*. Elsevier Science (USA); and Meade et al. (1999). "Expression of recombinant proteins in the milk of transgenic animals in Gene expression systems: using nature for the art of expression." J. M. Fernandez and J. P. Hoeffler ed., Academic Press. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the methods described by Shepherd et al, Monoclonal Antibodies: A Practical Approach (Oxford University Press, 2000).

The term "monoclonal antibodies" also includes "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. For example, the ability to bind to alpha-4 integrin. The "monoclonal antibodies" may also be isolated from phage antibody libraries using the techniques described for example in Clackson et al., 1991 Nature 352: 624-628 and Marks et al., 1991 J. Mol. Biol., 222: 581-597. "Humanized" forms of non-human (e.g., murine, rabbit, bovine, equine, porcine, and the like) antibodies are chimeric immunoglobulins, immunoglobulin chains or fragments thereof (such as Fv, Fab, Fab', F(ab')$_2$ or other antigen-binding subsequences of antibodies), which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

II. MICROSTRUCTURE ARRAYS

A. Microstructure Array Composition

Provided herein are compositions and methods for transdermal administration of a therapeutic polypeptide using an array of microprojections. General features of microstructure arrays suitable for use in the instant arrays and methods are described in detail in U.S. Patent Publication No. 2008/0269685, U.S. Patent Publication No. 2009/0155330, U.S. Patent Publication No. 2011/0006458, and U.S. Patent Publication No. 2011/0276028, the entire contents of which are explicitly incorporated herein by reference.

Generally, the number of microstructures in the array is preferably at least about 50, at least about 100, at least about 500, at least about 1000, at least about 1400, at least about 1600, or at least about 2000. For example, the number of microstructures in the array may range from about 1000 to about 4000, or from about 2000 to about 4000, or from about 2000 to about 3500, or from about 2200 to about 3200. The area density of microstructures, given their small size, may not be particularly high, but for example the number of microstructures per cm$^2$ may be at least about 50, at least about 250, at least about 500, at least about 750, at least about 1000, at least about 2000, or at least about 3000.

While the array itself may possess any of a number of shapes, the array is generally sized to possess a diameter of from about 5 millimeters (mm) to about 25 mm, or from about 7 mm to about 20 mm, or from about 8 mm to about 16 mm. Exemplary diameters include 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, and 25 mm.

The sizes of the microneedles and other protrusions for use with this invention will be a function of the manufacturing technology and of the precise application. In general, however, microstructures and other microprotrusions used in practice may be expected to have a height of at least about 20 μm to about 1000 μm, more preferably from about 50 μm to about 750 μm and most preferably from about 100 μm to about 500 μm. In specific, but not limiting embodiments, the microstructures have a height of at least about 100 μm, at least about 150 μm, at least about 200 μm, at least about 250 μm, or at least about 300 μm. In general it is also preferred that the microprojections have a height of no more than about 1 mm, no more than about 500 μm, no more than about 300 μm, or in some cases no more than about 200 μm or 150 μm. Often it will be desired that the microprotrusions will be long enough to penetrate at least partially through the stratum corneum layer of skin at some suitable point of application on the human body, for example the thigh, hip, arm, or torso. The microprojections may have an aspect ratio of at least 3:1 (height to diameter at base), at least about 2:1, or at least about 1:1.

The microprojections may have any suitable shape including, but not limited to polygonal or cylindrical. Particular embodiments include pyramidal including a four-sided pyramid, a funnel shape, a cylinder, a combination of funnel and cylinder shape having a funnel tip and a cylindrical base, and a cone with a polygonal bottom, for example hexagonal or rhombus-shaped. Other possible microprojection shapes are shown, for example, in U.S. Published Patent App. 2004/0087992 and in U.S. Application No. 61/745,513 filed Dec. 21, 2012. Microprojections may in some cases have a shape which becomes thicker towards the base, for example microprojections which have roughly the appearance of a funnel, or more generally where the diameter of the microprojection grows faster than linearly with distance to the microprojection distal end. It will be appreciate that polygonal microprojections may also have a shape which becomes thicker toward the base or where a radius or diameter grows faster than linearly with distance to the microprojection distal end. Where microprojections are thicker towards the base, a portion of the microprojection adjacent to the base, which may be called the "foundation," may be designed not to penetrate the skin.

Figure 1B:
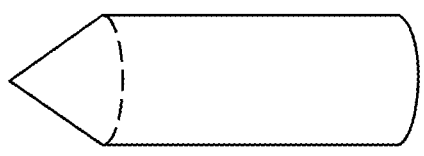
Figure 1A:
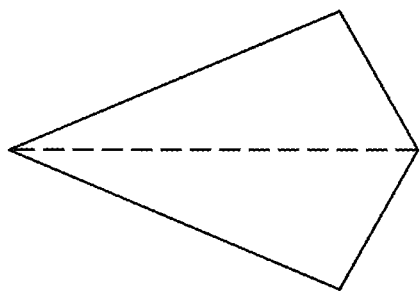

One illustrative shape for the microstructures is a cone with a polygonal bottom, for example, being hexagonal or rhombus-shaped. Additional microstructure shapes include those provided, for example, in U.S. Patent Publication No. 2004/0087992. In embodiments, at least a portion of the microstructure shape may be substantially cylindrical, cone-shaped, funnel-shaped, or pyramidal. In further embodiments, at least a portion of the microstructures has an asymmetrical cross-dimensional shape. Suitable asymmetric shapes include, but are not limited to, rectangular, square, oval, elliptical, circular, rhombus, triangular, polygonal, star-shaped, etc. In some embodiments, the distal layer has a cross-dimension in one direction that is smaller than the cross-dimension in the other direction. Exemplary cross-dimensional shapes with this configuration include, but are not limited to, rectangular, rhombus shaped, ellipse, and oval (see FIGS. 1A-1C for examples). It will further be appreciated that different portions and/or layers of a microstructure may have different cross-dimensional shapes. At least a portion of the microstructures may include one or more blade or piercing elements along its length and/or at the distal tip.

Figure 2A:
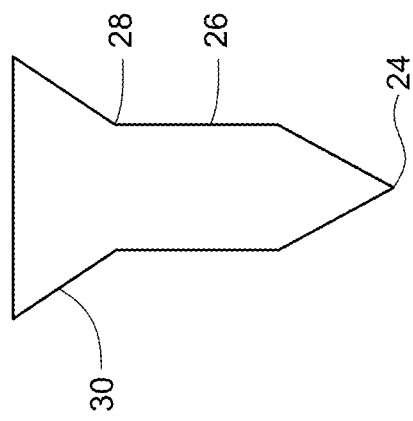
FIGS. 2A-2B are illustrations of exemplary shapes for microstructures including a funnel shape.
Figure 2B:
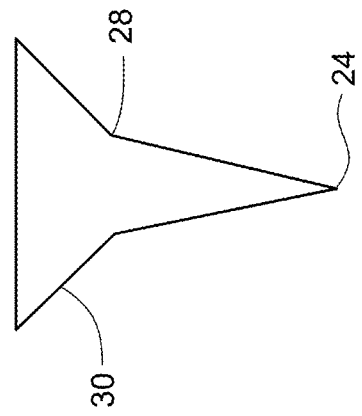

Microstructure shape can be understood in terms of a tip, a shank and a funnel. The angle at the tip is the apex angle—included angle by the planes or cone—and can have values from about 5 degree to about 60 degrees. The straight or substantially straight shank may or may not be present in a particular microstructure design. At the base of the shank or tip, towards the distal end, the included angle has a discontinuity or a point of inflection. The included angle jumps to take on a value greater than the apex angle for a shank-less tip and to greater than 0 degrees for microstructures with a shank. Portions of the microstructure beyond this point of inflection may be referred to as a "funnel". FIGS. 2A and 2B show examples of cross sectional elevation of the microstructures delineating different regions including the tip 24, shank 26, inflection point or edge 28 and the funnel 30. In FIG. 2B, the diameter of the microstructure is growing faster than linear fashion with respect to the distance from the distal end. Where microstructures are thicker towards the base, a portion of the microstructure adjacent to the base, which may be referred to herein as a "proximal portion" "backing portion", "basement", "foundation", or as an "upper portion", may be designed not to penetrate the skin.

The proximal funnel shape allows for relatively larger volumes to be dispensed in the microstructure mold for a given total length of the microstructure. The proximal funnel shape provides a larger volume (to fill) without requiring a proportional increase in microstructure height, which results in a longer drug containing portion in the microstructure. Thus, the proximal funnel shape allows for a larger solid volume for the distal portion of the microstructure with a single fill of the mold. Other shapes may require several fill and dry cycles to achieve the same amount of solid distal portion as one fill and dry cycle for the funnel shaped microstructures.

In one exemplary embodiment, at least a portion of the microstructures have a cylindrical funnel shape as shown in the array of FIG. 2B. As seen in the image, microstructures with this shape have a cylindrical shank and a funnel at the proximal end. In this embodiment, the distal tips of the microstructures typically, but not always, have a sharp, pointed or conical distal end to ease and/or facilitate penetration. The microstructures further have a funnel shape at the proximal end and a cylindrical shank between the distal and proximal ends.

The funnel portion may also be used to limit the depth of penetration. Since the funnel has a several times higher volume per unit height than the tip or shank, it also requires several times higher energy to penetrate per unit depth than the tip or shank. Hence for a given energy, the microstructure would typically penetrate no more than the length of the tip and shank. The funnel thus effectively acts as the design element in the microstructure that limits the depth of penetration thereby ensuring tolerable sensation.

In embodiments, the microstructures have a sharp point or tip. A tip diameter of less than about 5 µm or 2 µm may be desirable. A tip diameter of less than about 1.5 µm is preferred, as is a tip diameter of less than about 1 µm.

The microprojections may be spaced about 0-500 µm apart. In specific, but not limiting embodiments, the microprojections are spaced about 0 µm, about 50 µm, about 100 µm, about 150 µm, about 200 µm, about 250 µm, about 300 µm, about 350 µm, about 400 µm, about 450 µm, or about 500 µm apart. The space between the microprojections may be measured from the base of the microprojections (base to base) or from the tip (tip to tip).

In further embodiments, at least a portion of the microprojections may be detachable from the microprojection array. Detachable microprojection arrays are described in U.S. Patent Publication 2009/0155330 and in U.S. Patent Application No. 61/745,513 filed Dec. 21, 2012, each of which is incorporated herein by reference. Detachable microprojection arrays may be accomplished by a number of approaches including, but not limited to, a layered approach in which the array is composed of multiple layers, and a layer comprising the areas where the microprojections attach to the base of the array is more readily degradable than other layers.

One potential advantage of detaching microprojections is elimination of sharp disposal requirements. Another potential advantage of detaching microprojections is elimination of needle stick injury. Another potential advantage of detaching microprojections is elimination of misuse, for example needle sharing, since the substrate without microprojections or with microprojections whose tips have been blunted due to biodegradation will not penetrate the skin. Another potential advantage of detaching microprojections is the avoidance of drug misuse because drug enriched tips are dissolved in the skin and no or minimal drug is left in the array.

Alternatively, an array made of a homogeneous material may be employed, in which the material is more readily degradable at lower pH's. Arrays made of such a material will tend to degrade more readily near the attachment points because these, being closer to the surface of the skin, are at a lower pH than the distal ends of the microprojections. (The pH of the skin's surface is generally lower than that of the skin further inwards, pH being for example approximately 4.5 on the surface and approximately 6.5 to 7.5 inward).

Materials whose solubility is dependent on pH can be, for example, insoluble in pure water but dissolve in acidic or basic pH environment. Using such materials or combination of materials, the arrays can be made to differentially biodegrade at the skin surface (pH approximately 4.5) or inside the skin. In the former, the whole array can biodegrade while in the latter, the microprojection portion of the array will biodegrade allowing the base substrate to be removed and discarded.

Materials whose degradability in an aqueous medium is dependent on pH may be made, for example, by utilizing the acrylate copolymers sold by Rohm Pharma under the brand name Eudragit, which are widely used in pharmaceutical formulation. A further example of a material with pH-dependent solubility is hydroxypropyl cellulose phthalate. Materials with pH-dependent solubility have been developed, for example, for use as enteric coatings in oral dosage forms. See, e.g., U.S. Pat. No. 5,900,252 and *Remington's Pharmaceutical Sciences* (18th ed. 1990).

It may also be desirable for the microprojection array of the invention to comprise one or more additional layers in addition to the layer which comprises the therapeutic agent. There are a number of reasons why arrays with multiple layers may be desirable. For example, it is often desirable that, compared to the whole volume of the microprojection array, the microprojections themselves have a higher concentration of active ingredient. This is so, for example, because the microprojections can be expected in many cases to dissolve more rapidly, being in a more hydrated environment than the base of the array. Furthermore, in some protocols for array application, the array may be left in for a short period of time during which essentially only the microprojections can dissolve to a substantial extent. The desirability of placing a higher concentration of active in the projections themselves is particularly acute when the active is costly. A way to achieve a higher concentration of active in the projections themselves is to have a first active-containing layer which includes the microprojections or a substantial proportion of the microprojections, and a second layer with a reduced or zero concentration of active which includes the base or a substantial proportion of the base.

B. Manufacturing Microprojection Arrays

Microprojection arrays as described herein may be fabricated by the techniques for the fabrication of two-layer arrays which are disclosed in U.S. Patent Publication No. 2008-0269685. The application of these techniques in the context of polypeptides is summarized here.

In general, an array is prepared by (a) providing a mold with cavities corresponding to the negative of the microprotrusions, (b) filling the mold with a casting solution comprising a pharmaceutically active agent and a solvent, (c) removing the solvent, and (d) demolding the resulting array from the mold. In one or more embodiments, the microprojections themselves comprise the active agent, as opposed to having the active agent present as a coating on a microprojection or microneedle made of a biocompatible material such as a metal.

The microstructure of the microstructure arrays referred to, for example, in U.S. Patent Publication No. 2008/0269685, U.S. Patent Publication No. 2009/0155330, U.S. Patent Publication No. 2011/0006458, and U.S. Patent Publication No. 2011/0276028 is usually comprised of polymer, excipients and the pharmaceutically active agent (API). A structure-forming polymer is added to provide mechanical strength and structure stability to the microprojections, enabling the microstructure to penetrate the skin. The polymer is also biocompatible, as well as inert to most APIs.

At least a portion of the microstructures as described in the patent publications referred to above is formed of a biodegradable, bioerodible, bioabsorbable and/or biocompatible polymer matrix. Biocompatible, biodegradable, bioabsorbable and/or bioerodible structure-forming polymers for use in the described microprojection arrays include poly(lactic acid) (PLA), poly(glycolic acid) (PGA), poly(lactic acid-co-glycolic acid)s (PLGAs), polyanhydrides, polyorthoesters, polyetheresters, polycaprolactones (PCL), polyesteramides, poly(butyric acid), poly(valeric acid), polyvinylpyrrolidone (PVP), polyvinyl alcohol (PVA), polyethylene glycol (PEG), block copolymers of PEG-PLA, PEG-PLA-PEG, PLA-PEG-PLA, PEG-PLGA, PEG-PLGA-PEG, PLGA-PEG-PLGA, PEG-PCL, PEG-PCL-PEG, PCL-PEG-PCL, copolymers of ethylene glycol-propylene glycol-ethylene glycol (PEG-PPG-PEG, trade name of Pluronic® or Poloxamer®), dextran, hetastarch, tetrastarch, pentastarch, hydroxyethyl starches, cellulose, hydroxypropyl cellulose (HPC), sodium carboxymethyl cellulose (Na CMC), thermosensitive HPMC (hydroxypropyl methyl cellulose), polyphosphazene, hydroxyethyl cellulose (HEC), other polysaccharides, polyalcohols, gelatin, alginate, chitosan, hyaluronic acid and its derivatives, collagen and its derivatives, polyurethanes, and copolymers and blends of these polymers. A preferred hydroxyethyl starch for this use has a degree of substitution of in the range of 0-0.9.

The biodegradability or dissolvability of the microprojection arrays as described in the above-referenced patent publications may be facilitated by the inclusion of one or more sugar. Exemplary sugars include dextrose, fructose, galactose, maltose, maltulose, iso-maltulose, mannose, lactose, lactulose, sucrose, and trehalose. Sugar alcohols, for example lactitol, maltitol, sorbitol, and mannitol, may also be employed. Cyclodextrins can also be used advantageously in microneedle arrays, for example α, β, and γ cyclodextrins, for example hydroxypropyl-β-cyclodextrin and methyl-β-cyclodextrin. Sugars and sugar alcohols may also be helpful in stabilization of peptides and proteins and in modifying the mechanical properties of the microprojections by exhibiting a plasticizing-like effect.

The biodegradability of a microstructure array as described in the above-referenced patent publications may also be facilitated by inclusion of water-swellable polymers such as crosslinked PVP, sodium starch glycolate, crosslinked polyacrylic acid, crosscarmellose sodium, celluloses, natural and synthetic gums, polysaccharides, or alginates. In a multilayer array, the sugars and other polymers which facilitate biodegradability may be located only in a layer or layers which encompass the microprojections. These polymers may also be used as structure-forming polymers.

Further, the structure-forming polymers used in a microstructure array as described in the above-referenced patent publications may possess a variety and range of molecular weights. The polymers may, for example, have molecular weights of at least about 1K Da, at least about 5K Da, at least about 10K Da, at least about 20K Da, at least about 30K Da, at least about 50K Da, or at least about 100K Da. Where the microstructure is meant to be biodegradable, it may be desired to have biodegradable portion(s) comprise one or more polymers having a lower molecular weight. The strength-molecular weight relation in polymers is an inverse relation so structure-forming polymers with lower molecular weights have a lower strength and will tend to be more biodegradable. Further polymers with a lower molecular weight will be more likely to break due to the lower strength. In embodiments described in the above-reference patent publications, at least the distal layer comprises at least one structure-forming polymer having a lower molecular weight. In an embodiment, at least the distal layer comprises at least one structure-forming polymer having a molecular weight less than about 100K Da. In another embodiment, at least the distal layer comprises at least one structure-forming polymer having a molecular weight less than about 20K Da. In other embodiments, at least the distal layer comprises at least one structure-forming polymer having a molecular weight less than about 1K Da, less than about 5K Da, less than about 10K Da, less than about 15K Da or less than about 20K Da. In one embodiment, at least the distal layer comprises at least one structure-forming polymer having a molecular weight of between about 1K-100K Da or between about 1K-20K Da. In other embodiments, the distal layer comprises at least one structure-forming polymer having a molecular weight of between about 1K-100K Da, between about 1000-5000 Da, between about 1000-10,000 Da, between about 1000-15,000 Da, between about 5000-10,000 Da, between about 5000-15,000 Da, between about 5000-20,000 Da, between about 10,000-15,000 Da, between about 10,000-20,000 Da, and between about 15,000-20,000 Da.

Nevertheless, the polymer may sometimes not be compatible with a particular API, resulting in difficult challenges for loading such APIs. For this reason it is desirable to develop a structure-forming polymer-free microstructure which may be used for formulation of APIs which are incompatible with polymers in use for microstructure arrays as described above.

III. MICROSTRUCTURE ARRAYS WITH STRUCTURE-FORMING POLYMER-FREE MICROSTRUCTURE

A. Structure-Forming Polymer-Free Microstructure Compositions

As described in more detail below, it was unexpectedly found that formulation of a polymer-free microstructure is capable of forming a solid microstructure with mechanical strength sufficient for penetrating skin if the API has a high enough molecular weight. Such microstructures are formulated using a solution of a high molecular weight macromolecule in solution with a stabilizing excipient such as sorbitol, sucrose, or trehalose. In some embodiments, a macromolecule solution is lyophilized then reconstituted with water containing a surfactant (e.g., Polysorbate 20) to a formulation with a macromolecule concentration greater than about 200 mg/ml.

Importantly, without adding any of the structure-forming polymers described above with reference to U.S. Patent Publication No. 2008/0269685, U.S. Patent Publication No. 2009/0155330, U.S. Patent Publication No. 2011/0006458, and U.S. Patent Publication No. 2011/0276028, to the polypeptide solution, before or after lyophilization and reconstitution, the casting solution dispensed into the microarray mold will produce a microstructure capable of penetrating the skin and administering the macromolecule. More specifically, the distal layer of the microstructure does not comprise a structure-forming polymer.

The structure-forming polymer-free microstructures as described in more detail below are able to release the incorporated macropolymer into a subcutaneous layer over an extended period of time.

In a preferred embodiment, the macromolecule is a polypeptide or peptide. Glycosylation of the polypeptide to peptide may increase the molecular weight and may impart structural and/or mechanical strength of the microstructure into which the macromolecule is formulated.

It is thought that the high molecular weight structure of the macromolecule provides the necessary mechanical strength to the microstructure. Such polypeptides may have a molecular weight of at least 100,000 Daltons (Da), or between about 100,000 Da and about 1,000,000 Da.

Alternatively, smaller polypeptides (peptides), having a molecular weight of about 10,000 Da to about 100,000 Da, may be formulated into the microstructures. In some embodiments, these peptides are glycosylated to produce an API with a larger molecular weight and molecular radius, thereby imparting the necessary mechanical strength to the microstructure.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Examples of peptides and proteins which may be used with the microstructure arrays include, but are not limited to, parathyroid hormone (PTH), oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof. Administration of oligonucleotides is also contemplated, and includes DNA and RNA, other naturally occurring oligonucleotides, unnatural oligonucleotides, and any combinations and/or fragments thereof. Currently marketed therapeutic antibodies include but are not limited to Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

The polypeptide solution generated to make a polypeptide casting or molding solution may have a polypeptide concentration of at least 10 mg/ml to about 400 mg/ml.

The polypeptide solution containing the therapeutic polypeptide may comprise a stabilizing excipient, including but not limited to, polyols, sugars, amino acids, amines, and salting out salts. Sucrose and trehalose are the most frequently used sugars and large polyols are in general better stabilizers than smaller polyols. Additional sugars which may be used include, but are not limited to, fructose and dextrose. Hydrophilic polymers, such as polyethylene glycols (PEGs), polysaccharides, and inert proteins, are used to non-specifically to stabilize proteins and enhance protein assembly. Examples include dextran, hydroxyl ethyl starch (HETA), PEG-4000, and gelatin. Smaller PEGs have been found to be less effective than larger ones. Additionally, non-polar moieties on certain polymers such as PEGs and Pluronics can decrease water surface tension rendering them as surfactants that suppress surface adsorption induced aggregation. Non-ionic surfactants are widely used to stabilize proteins, suppress aggregation, and assist in protein refolding. Polysorbate 80 and Polysorbate 20, also known as Tween 80 and Tween 20, respectively, have been widely incorporated in marketed protein pharmaceuticals at 0.0003-0.3% range. Other examples include Brij 35, Triton X-10, Pluronic F127, and sodium doceyl sulfate (SDS). Amino acids. These excipients stabilize proteins by a variety of mechanisms. Examples include histidine, arginine, and glycine. Other amino acids used as formulation excipients include methionine, proline, lysine, glutamic acid, and arginine mixtures.

B. Methods for Making Structure-Forming Polymer-Free Microstructures

The microarray microstructures are constructed using a solution of a polypeptide. The solution is preferably an aqueous solution which may be buffered, such as with a phosphate buffered saline at a pH of about 5.0 to 8.0, or about 6.5 to 7.5, which helps to preserve the native structure of the polypeptide. Alternatively, the solution is buffered with a histidine buffer, with a pH of about 5.0 to 7.0 or 5.5 to 6.5 or about 6.0. In some embodiments, a stabilizing excipient such as a sugar is added to the solution. When concentrations greater than about 100 mg/ml or 200 mg/ml are desired for therapeutically effective administrations, the solution may be lyophilized and reconstituted in an appropriate volume of a buffered aqueous solution. Reconstitution of the lyophilized polypeptide composition may be done in water for injection which contains a surfactant such as Polysorbate 20 or Polysorbate 80. The polypeptide solutions for casting may further comprise an antioxidant such as ethylenediaminetetraacetic (EDTA), glutathione, methionine, cysteine, D-alpha tocopherol aceta, vitamin E or ascorbic acid. Suitable components are nontoxic to recipients at the dosages and concentrations employed. Further examples of components that may be employed in pharmaceutical formulations are presented in Remington's Pharmaceutical Sciences, $16^{th}$ Ed. (1980) and $20^{th}$ Ed. (2000), Mack Publishing Company, Easton, Pa.

The polypeptide casting composition is then dispensed over a microstructure mold and dried in a chamber having a relative humidity of at least about 10%. In some preferred embodiments, the relative humidity is about 80% to 90%. This chamber is set at a temperature ranging from about 20° C. to 50° C. but is preferably about 25° C. to 30° C. The mold is then dried in an oven set at about 5° C. to 50° C., or more generally about 30° C. to 35° C. The oven may dry the mold via convention, conduction or radiation heat.

When the microstructure arrays comprising the structure-forming polymer-free microstructures formulated with a macromolecule are administered to the skin of a mammal, the microstructures have the structural and mechanical strength sufficient to allow each microstructure to penetrate the skin at an efficiency which is at least as efficient as a microstructure formulated with a structure-forming polymer as described in previous patent publications detailed above. The final microstructure array when fabricated as described herein contains about 1 mg to 25 mg, 2 mg to 20 mg, 5 mg to 15 mg, 1 mg to 10 mg, 2 mg to 80 mg, 4 mg to 5 mg, 5 mg to 10 mg, 10 mg to 20 mg, 10 mg to 15 mg, 13 mg to 17 mg, 15 mg to 20 mg, or 5 mg to 15 mg of the macromolecule for administration to a subject.

Importantly, the macromolecules formulated within the structure-forming polymer-free microstructures remain stable and therapeutically effective. Stability of the released macromolecule may be measured using a variety of methods, including but not limited to, measurement of aggregation and oxidation. To measure aggregation, macromolecules released by or extracted from structure-forming polymer-free microstructures are analyzed for the formation of high molecular mass species using size exclusion high performance liquid chromatograph (SEC-HPLC). Oxidation of methionine residues are monitored using, for example, a Lys-C proteolysis mapping assay and reverse phase HPLC.

IV. METHODS OF USE

The methods, kits, microstructure arrays and related devices described herein may be used for treating any condition. It will be appreciated that the microstructure arrays may be used with any appropriate applicator including the applicator described in U.S. Publication No. 2011/0276027, which is incorporated by reference herein in its entirety.

V. EXAMPLES

The following examples are illustrative in nature and are in no way intended to be limiting. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

Formulating a Microstructure with a Monoclonal Antibody

A solution containing a monoclonal antibody is mixed with a stabilizing excipient such as sucrose or trehalose to form an antibody concentration of about 50 mg/ml to 100 mg/ml. To create a solution with a monoclonal antibody concentration greater than about 100 mg/ml or 200 mg/ml, the solution is lyophilized, then reconstituted with water for injection (WFI) containing a surfactant such as sorbitol for drug-in-tip (DIT) formulations for casting microstructures.

About 75 μL of liquid DIT formulation is dispensed on a silicone mold, covered with a 22 mm×30 mm glass cover slip to spread the formulation on the mold, and then pressurized for 1 minute at about 40 to 60 psi. The formulation is then wiped and the mold dried in a chamber with about 80% to 90% relative humidity (RH), at room temperature for about 10 to 15 minutes. The mold is then incubated for about 30 minutes in an oven at about 30° C. to 35° C. A polylactide-co-glycolide (PLGA) layer is then casted onto array to connect the microstructures.

The construct is dried in a compressed dry air box for about 30 minutes, and then in a convection oven at about 40° C. to 50° C. for about 30 minutes.

UV adhesive is then dispensed on the top of the PLGA layer, covered with 5 ml polycarbonate (PC) film to spread the adhesive, and then cured using a UV Fusion system. The UV curing dose is about 1.6 J/cm². After curing the microstructure array comprising the DIT layer, PLGA layer, and UV adhesive backing layer on PC, the structure is die cut with an 11 mm or 16 mm punch. The microstructure array is dried under full vacuum at room temperature overnight followed by full vacuum at about 30° C. to 40° C. for 6 hours. The microstructures were pouched individually with desiccant in polyfoil pouches.

Example 2

Monoclonal Antibody Stability within the Microstructure

Effects of the microstructure formulation on stability of the monoclonal antibody are assessed by measuring oxidation of methionine residues in the monoclonal antibody. This is done by Lys-C proteolytic mapping using reverse phase HPLC.

Monoclonal antibody is extracted from the microstructure by submerging the microstructure in 20 mM acetate buffer with 0.05% Tween 20 for approximately 1 hour on a low speed shaker. The extraction is analyzed by Lys-C proteolysis and size exclusion high performance liquid chromatography (SEC-HPLC) for monitoring aggregation.

Changes in High Molecular Mass species (HMMs) and methionine oxidation are monitored over 4 weeks at 5° C., 25° C. and 40° C. If the monoclonal antibody remains stable when formulated as described above, there will be no significant increase in HMMs of the monoclonal antibody, compared to the initial material (API bulk).

Example 3

In Vitro Skin Penetration Efficiency

Experiments are performed to assess the mechanical strength and penetration efficiency of the microstructure arrays formulated as described in Example 1. In vitro performance is characterized by the microstructure array's ability to penetrate excised pig skin as compared to a microstructure array fabricated using structure-forming polymers.

Full-thickness pig skin is excised from the abdomen and then clipped and shaved to remove hair bristles. Microstructure arrays are applied to shaved skin sites using a reusable application and held by hand in situ for about 5 to 15 minutes. Application sites are stained and photographed to visualize the microstructure penetrations. Penetrations are quantified using a custom developed image analysis program. Skin penetration efficiency (SPE) is then calculated based on the theoretical number of microstructures expected for the constructed microstructure array as follows:

% SPE=100×(no. penetrations/no. microstructures)

If the microstructure arrays fabricated with and without structure-forming polymers show equivalent SPE, it can be concluded that microstructure arrays having microstructures void of structure-forming polymers are equivalently strong and effective as those having a microstructure containing a structure-forming polymer.

In vitro skin penetration efficiency experiments can also be done to compare the strength of microstructures in the presence of difference stabilizing excipients. Microstructure arrays are fabricated as described above in which microstructures are formulated with either sucrose or trehalose as a protein stabilizer. The arrays are then applied to shaved skin sites on pig skin using a reusable application and held by hand in situ for about 5 to 15 minutes. Equally excellent SPE using both arrays indicate that strong mechanical strength is achieved when using different sugars as the stabilizing excipient.

The effects of humidity on skin penetration efficiency is also tested is a similar manner as above. The microstructure arrays are exposed to 65% relative humidity for 10 minutes. The SPE of microstructure arrays which are or are not exposed to 65% relative humidity are then compared. If both arrays have a high SPE (e.g., greater than 80%), this indicates that the microstructure array, even in the absence of structure-forming polymer, is mechanically strong, even after exposure to a humid environment. Like structure-forming polymer-containing microstructure arrays, the polymer-free microstructure arrays have both good mechanical performance and high humidity tolerance.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

Example 4

Formulating a Microstructure with a Polypeptide

A solution containing a polypeptide is mixed with either sucrose or trehalose as a stabilizing excipient. The solution is then lyophilized and reconstituted with water for injection (WFI) containing Polysorbate 20 (PS20) to form a polypeptide casting solution with a polypeptide concentration greater than 200 mg/ml for casting the microstructures.

About 75 µL of liquid DIT formulation is dispensed on a silicone mold, covered with a 22 mm×30 mm glass cover slip to spread the formulation on the mold, and then pressurized at 50 psi for 1 minute. The formulation is then wiped and the mold dried in a chamber with 85% relative humidity (RH), at room temperature for 10 minutes. The mold was then incubated for about 30 minutes in an oven at 32° C. A polylactide-co-glycolide (PLGA) layer was casted on the array to connect the microstructures.

The construct is dried in a compressed dry air box for 30 minutes, and then dried by convection, conduction or radiation at 45° C. for 30 minutes.

UV adhesive is then dispensed on the top of the PLGA layer, covered with 5 ml polycarbonate (PC) film to spread the adhesive, and then cured using a UV Fusion system. The UV curing dose is about 1.6 J/cm². After curing the microstructure array comprising the DIT layer, PLGA layer, and UV adhesive backing layer on PC, the structure was die cut with an 11 mm or 16 mm punch. The microstructure array is dried under full vacuum at room temperature overnight followed by full vacuum at 35° C. for 6 hours. The microstructures are pouched individually with desiccant in polyfoil pouches.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

What is claimed is:

1. A microstructure apparatus, comprising:
    a backing having a first surface and a second surface opposed thereto; and
    a microstructure array comprising a plurality of microstructures extending outwardly from the first surface of the backing;
    each microstructure in the plurality of microstructures comprising a biodegradable distal layer and at least one proximal layer positioned between the distal layer and the first surface of the backing;
    wherein the distal layer comprises between about 50-90% by weight of a therapeutic macromolecule and a stabilizing excipient, and wherein the distal layer does not comprise a structure-forming polymer.

2. The microstructure apparatus of claim 1, wherein the macromolecule is selected from the group consisting of a polypeptide, a protein, and a monoclonal antibody.

3. The microstructure apparatus of claim 1, wherein the macromolecule is glycosylated.

4. The microstructure apparatus of claim 1, wherein the macromolecule is present in each of the plurality of microstructures in an amount of about 0.05 µg to 5 µg.

5. The microstructure apparatus of claim 1, wherein the stabilizing excipient is a sugar.

6. The microstructure apparatus of claim 1, wherein the distal layer further comprises a surfactant.

7. The microstructure apparatus of claim 6, wherein the surfactant is present at a concentration of about 0.01% by weight to 1.0% by weight.

8. The microstructure apparatus of claim 1, wherein the distal layer further comprises an antioxidant.

9. The microstructure apparatus of claim 1, wherein the macromolecule has a molecular weight of between about 10,000 Daltons to 1,000,000 Daltons.

10. A microstructure apparatus comprising:
a backing having a first surface and a second surface opposed thereto; and
a microstructure array comprising a plurality of microstructures extending outwardly from the first surface of the backing;
each microstructure in the plurality of microstructures comprising a biodegradable polymer-free distal layer and at least one proximal layer positioned between the polymer-free distal layer and the first surface of the backing;
wherein the polymer-free distal layer is comprised of between about 50-90% by weight of a therapeutic macromolecule with a molecular weight of between about 10,000 Daltons to 1,000,000 Daltons and a balance of a stabilizing excipient and, optionally, an antioxidant.

11. The microstructure apparatus of claim 10, wherein the at least one therapeutic macromolecule has a molecular weight of between about 100,000 Daltons to 1,000,000 Daltons.

12. The microstructure apparatus of claim 10, wherein the macromolecule is selected from the group consisting of a polypeptide, a protein, and a monoclonal antibody.

13. The microstructure apparatus of claim 10, wherein the macromolecule is glycosylated.

14. The microstructure apparatus of claim 10, wherein the macromolecule is present in each of the plurality of microstructures in an amount of about 0.05 µg to 5 µg.

15. The microstructure apparatus of claim 10, wherein the stabilizing excipient is a sugar.

16. The microstructure apparatus of claim 10, wherein the stabilizing excipient is a surfactant.

17. The microstructure apparatus of claim 16, wherein the surfactant is present in the distal layer at a concentration of about 0.01% by weight to 1.0% by weight.

18. The microstructure apparatus of claim 10, wherein the distal layer comprises an antioxidant.

* * * * *